United States Patent [19]

Chaoui

[11] Patent Number: 4,702,240

[45] Date of Patent: Oct. 27, 1987

[54] DEMAND-RESPONSIVE GAS BLENDING SYSTEM FOR MEDICAL VENTILATOR

[75] Inventor: Samir M. Chaoui, Riverside, Calif.

[73] Assignee: Bear Medical Systems, Inc., Riverside, Calif.

[21] Appl. No.: 888,776

[22] Filed: Jul. 22, 1986

[51] Int. Cl.$^4$ .............................................. A62B 7/00
[52] U.S. Cl. ........................ 128/204.18; 128/204.28; 128/205.11; 128/205.13; 128/205.18; 128/205.24
[58] Field of Search ................... 128/203.28, 203.29, 128/203.12, 204.18, 204.23, 204.26, 204.27, 204.28, 205.11, 205.13, 205.14, 205.15, 205.16, 205.17, 205.18, 205.24, 204.25; 137/625.4, 625.41

[56] References Cited

U.S. PATENT DOCUMENTS

| 2,581,450 | 1/1952 | Seeler | 128/204.25 |
| 2,897,833 | 8/1959 | Seeler | 128/205.11 |
| 3,087,707 | 4/1963 | Seeler | 128/204.27 |
| 3,768,468 | 10/1973 | Cox | 128/145.8 |
| 3,830,257 | 8/1974 | Metivier | 137/625.4 |
| 3,876,957 | 4/1975 | Veit et al. | 137/81 |
| 3,916,889 | 11/1975 | Russell | 128/145.8 |
| 4,036,253 | 7/1977 | Fegan et al. | 137/556 |
| 4,072,148 | 2/1978 | Munson et al. | 128/142.2 |
| 4,121,580 | 10/1978 | Fabish | 128/145.7 |
| 4,340,044 | 7/1982 | Levy | 128/204.21 |
| 4,587,967 | 5/1986 | Chu et al. | 128/204.21 |

Primary Examiner—Edward M. Coven
Assistant Examiner—J. P. Lacyk
Attorney, Agent, or Firm—Klein & Szekeres

[57] ABSTRACT

A gas blending system for use with a medical ventilator blends a pressurized gas with ambient air for delivery to the ventilator in response to the ventilator's demand for gas during the gas intake phase of its cycle. The system comprises a demand valve that discharges a flow of the pressurized gas in proportion to the demand applied to its outlet. The demand valve outlet is coupled to a first inlet of a blending valve, a second inlet of which is open to the atmosphere. The blending valve has a blended gas outlet adapted to be coupled to the ventilator. The total demand applied by the ventilator to the blended gas outlet is transmitted to the first and second inlets. A proportioning mechanism in the blending valve adjusts the demand that is transmitted to the demand valve outlet through the blending valve first inlet as a percentage of the total demand applied to the blended gas outlet. The total flow of blended gas from the blended gas outlet is proportional to the total demand applied thereto, while the percentage of pressurized gas in the blended gas flow is proportional to the ratio of the demand applied to the first inlet to the total demand applied to the blended gas outlet. The pressurized gas percentage is determined only by the proportioning mechanism, and is independent of the total applied demand.

27 Claims, 7 Drawing Figures

DEMAND-RESPONSIVE GAS BLENDING SYSTEM FOR MEDICAL VENTILATOR

BACKGROUND OF THE INVENTION

This invention relates broadly to the field of respiratory therapy equipment. More specifically, it relates to a system for blending breathable gases (e.g., air and oxygen) for delivery to a patient that is breathing with the assistance of a ventilator.

Patients that are breathing with the assistance of a ventilator often require the mixture of air with another gas. For example, many mechanically-ventilated patients require oxygen-enriched air. Consequently, many ventilators incorporate a mechanism or system for blending air and oxygen in adjustable proportions. See, for example, U.S. Pat. No. 4,072,148 to Munson et al.; U.S. Pat. No. 3,768,468 to Cox; U.S. Pat. No. 4,340,044 to Levy et al.; and U.S. Pat. No. 3,916,889 to Russell.

Recently, efforts to control medical costs have led to increasing use of so-called "home care" ventilators. Such ventilators are compact enough to be transportable, allowing many patients who are not critically ill to continue their respiratory therapy in their homes. These home care ventilators typically employ a reciprocating piston pump to deliver air to the patient in accordance with a prescribed flow rate-versus-time curve that is a function of several adjustable parameters, such as minute volume, respiratory rate, and inspiratory-to-expiratory time ratio, for example. While these relatively compact ventilators have many of the features of the larger, "critical care" ventilators used in hospitals, the requirement of transportability does impose some limitations. One such limitation, for example, has been the lack of a convenient means for oxygen has been the lack enrichment that would provide accurate control of the concentration of oxygen, and which would allow the concentration to remain substantially constant throughout the inspiratory stroke of the piston.

In the prior art, for example, oxygen is typically added to the delivered air flow downstream from the ventilator piston. The oxygen is typically supplied from a compressed gas tank or a flow-controlled source, such as an oxygen concentrator. There are, however, problems with this approach.

First, there is a problem with adequate mixing of the air and oxygen when the oxygen is added to the gas flow somewhere between the pump and the patient. Another important problem is the difficulty in maintaining a relatively constant percentage of oxygen throughout the inspiratory stroke of the piston. This latter problem has two sources: (1) the oxygen is supplied at a substantially constant flow, while the air flow from the piston is time-variable; and (2) the oxygen flow rate must be carefully readjusted whenever the flow parameters of the ventilator are changed.

The prior art has attempted to overcome these problems through the use of accumulators and labyrinthine flow paths to achieve gas mixing. Such mechanisms do little to address the constant proportion problem, and they "solve" the mixing problem at the expense of accuracy and repeatability. Moreover, they tend to "dump" excess oxygen to the atmosphere, which is not only wasteful, but which also poses a potential fire hazard.

Prior art gas blending mechanisms exist that address the problem of providing a constant blend proportion in the face of varying flow rates demanded by the ventilator. See, for example, U.S. Pat. No. 4,072,148 to Munson et al. Such mechanisms, however, are adapted for applications, such as in critical care ventilators, where the constituent gases are both supplied from pressure-regulated (and, preferably, pressure-balanced) sources. In home care ventilators, by contrast, the air is supplied to the ventilator from the ambient atmosphere, while the oxygen is supplied from a pressurized source. Therefore, blending mechanisms that need both gas sources pressure-regulated do not work in home care ventilators.

Still another problem associated with oxygen enrichment in a home care ventilator is that of oxygen wastage. Such ventilators require the use of relatively small oxygen cylinders, lest the purpose of transportability be defeated. This requirement militates against the use of oxygen dilution devices, of the type disclosed in U.S. Pat. No. 4,036,253 to Fegan et al., which blend air and oxygen by diluting a more or less constant flow of oxygen with an adjustable flow of air.

Accordingly, there has been a need for a gas blending system that is particularly adapted to home care ventilators of the piston pump type. Specifically, the need has been felt for a gas blending system that can be employed upstream of the pump to assure adequate gas mixing without wasting oxygen, and that accurately provides substantially constant proportions of the blended gases throughout the intake stroke of the piston pump. Such a system should also provide for convenient and accurate adjustment of the selected gas proportions. Furthermore, in the context of oxygen enrichment for a home care ventilator, such a blending system should minimize wasteful oxygen usage. These features should, advantageously, be provided in a system that is relatively simple to operate and maintain, and that can be conveniently employed as an "add-on" option with a wide variety of ventilators.

SUMMARY OF THE INVENTION

Broadly, the present invention is a gas blending system for use with a medical ventilator of the type having a gas pumping mechanism (e.g., a piston or a bellows) with a periodic inspiratory gas intake phase of operation, wherein the blending system blends two gases (e.g., air and oxygen) for delivery to the ventilator in response to the ventilator's demand for gas during the intake phase. The system blends a first gas (e.g., oxygen) supplied on flow demand from a pressure-regulated source, and a second gas (e.g., air) supplied at ambient pressure. The system comprises a demand valve receiving the first gas from the pressure-regulated source, and a blending valve having a first inlet coupled to the demand valve outlet, and a second inlet adapted to receive the second gas supplied at ambient pressure. The blending valve also includes a blended gas outlet adapted to be coupled to the gas intake port of the ventilator, and proportioning means for selectively adjusting the relative flow capacities of the first and second inlets.

In operation, the demand valve provides a flow of the first gas from its outlet in proportion to the demand experienced at its outlet. (In the context of this disclosure, the term "demand" is defined as a measure of negative, or sub-ambient, pressure; the greater the "demand", the more negative the pressure.) The experienced demand, in turn, is that which is communicated to the demand valve outlet from the ventilator gas intake port via the blending valve. The entire demand for gas expressed by the ventilator is thus communicated to the blending valve, substantially instantaneously. The total blended gas flow from the blending valve, which is the sum of the flows of the first and second gases into the blending valve's first and second inlets, respectively, is therefore proportional to the total instantaneous demand applied to the blending valve outlet by the ventilator. The proportioning means proportions this total demand between the two blending valve inlets, whereby the percentage of the total demand experienced by the first inlet (and, therefore, the demand valve outlet coupled to it) can be selectively varied between a minimum and a maximum. Specifically, when the proportioning means applies the minimum demand percentage to the first blending valve inlet, insufficient demand is applied to the demand valve to provide any significant flow of the first gas through it. Thus, substantially the entire flow through the blending valve outlet constitutes the second gas received from the second inlet. Conversely, when the proportioning means applies the maximum demand percentage to the first inlet, the flow of the first gas from the demand valve provides substantially all of the flow through the blending valve outlet. In either case, as mentioned above, the total outflow of blended gas from the blending valve is proportional to the substantially instantaneous demand from the ventilator, throughout the entire gas intake phase of the ventilator's cycle.

The present invention contemplates the use of any of several types of demand valves that are well-known in the art. The blending valve, on the other hand, is novel, and at least two preferred embodiments may be employed. In both embodiments, the proportioning means proportions the demand by the selective adjustment of the relative flow capacities of the first and second inlets. Specifically, the proportioning means maintains the first inlet open to a constant flow capacity while varying the flow capacity of the second inlet between maximum flow (fully open) and minimum flow (fully closed). When the second inlet is fully open, there is essentially no demand (a "null" demand) applied to the first inlet, since the open second inlet acts as a pneumatic "short circuit" to prevent any significant demand from being applied to the first inlet. Thus, with the second inlet fully open, the total blending valve flow is provided by the second gas flowing from the second inlet. Conversely, when the second inlet is fully closed, all of the demand is applied to the first inlet, so that the total gas flow is provided by the first gas flowing into the first inlet. As the proportioning means varies the second inlet from fully closed to fully open, the percentage of the total demand applied to the first inlet is decreased from its maximum to its minimum, with the proportion of the total blending valve output provided by the first gas correspondingly decreasing.

In one preferred embodiment, the proportioning means comprises a rotatable cam, a rod having a proximal end engaged against the cam, and occlusion means on the distal end of the rod. The occlusion means is moved between first and second positions by the rotation of the cam against the rod. The first position of the occlusion means leaves the second inlet fully open, while the second inlet is fully closed by the occlusion means when the latter is moved to its second position. The first inlet remains fully open in both positions.

In another preferred embodiment, the proportioning means comprises a rotatable, hollow, cylindrical barrel with a first orifice in its side wall that registers with the first inlet, and a second side wall orifice that is registrable with the second inlet. The hollow interior of the barrel defines an internal bore that is in fluid communication with the blending valve outlet. The barrel is rotatable between first and second positions. In the first position, the second orifice is in substantially complete registration with the first inlet to open the first inlet fully. In the second position, the second orifice is out of registration with the second inlet, so that the barrel side wall fully closes the second inlet. Throughout the rotation of the barrel between its first and second positions, the first orifice substantially maintains its registration with the first inlet, thereby keeping the first inlet open to whatever demand is available to it.

In both embodiments, it can be seen that while the total flow from the blending valve depends upon the total demand applied to it, the proportions of the constituent gases flowing into the blending valve through its two inlets are dependent only upon the setting of the proportioning means. The proportions in the outflowing blended gas mixture thus remain substantially constant, regardless of the changes in demand that occur during the gas intake phase of the ventilator.

With either embodiment, a sub-ambient relief valve is advantageously provided, either integrally with the blending valve, or immediately downstream from it. The sub-ambient relief valve opens to the atmosphere in response to a predetermined demand that is somewhat greater than the maximum demand applied to the blending valve at its maximum gas flow rate. This predetermined demand level is reached only when the second blending valve inlet is closed, and the flow of the first gas through the first inlet is partially or totally interrupted. The sub-ambient relief valve thus assures that the patient receives a life-sustaining flow of air if, for example, the first gas supply becomes depleted.

From the foregoing summary, it can be seen that the present invention provides a number of important advantages, as compared with prior art gas blending apparatus. For example, by blending the gases upstream from the piston pump, thorough mixing of the gases is provided within the ventilator itself, without the need for accumulators and labyrinthine flow paths. In addition, accurate control of the blended gas proportions is obtained, with these proportions, once selected by the operator, remaining substantially constant throughout the intake stroke of the ventilator. Furthermore, when the present invention is used to blend a pressurized gas (e.g., oxygen) with ambient air, the pressurized gas is consumed on demand only, thereby minimizing both wastage and potential safety problems resulting from leakage of the pressurized gas to the atmosphere. Moreover, these advantages are provided in a blending system that is simple to operate and to maintain, and that is readily adapted for use as an "add-on" option with a wide variety of ventilators, and particularly home care ventilators.

These and other advantages of the invention will be more readily appreciated from the detailed description which follows.

DETAILED DESCRIPTION OF THE INVENTION

Figure 1:
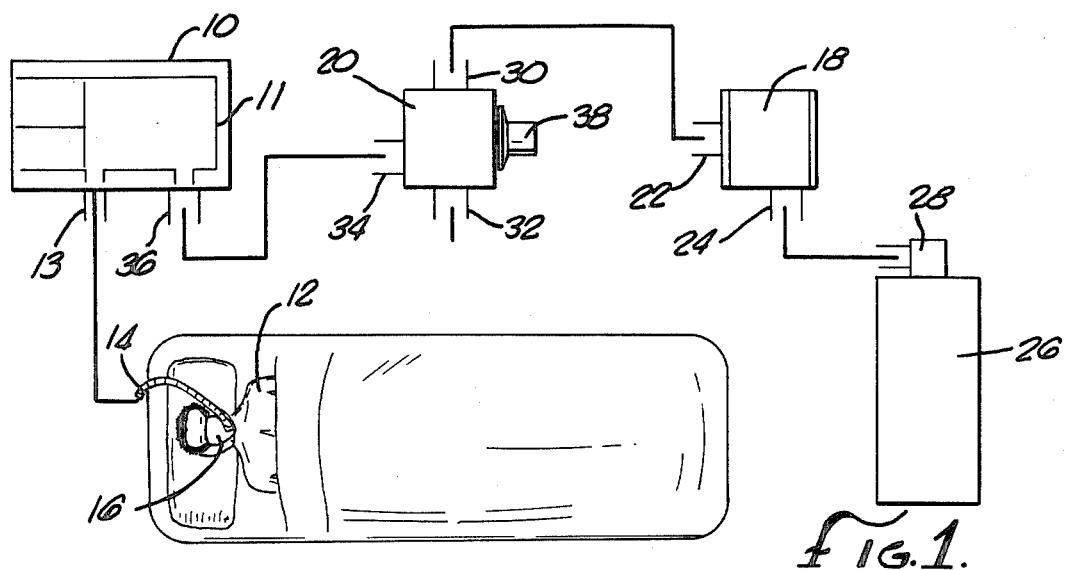
FIG. 1 is a schematic representation of a gas blending system in accordance with the present invention as employed with a medical ventilator.

FIG. 1 illustrates, schematically, the major elements of the present invention as used in conjunction with a medical ventilator 10. The ventilator 10 may be any commercially-available ventilator of the type that employs a piston pump 11 to force respiratory gas into the lungs of a patient 12 through an outlet 13, a conduit 14, and a patient connection, such as a mask 16. Reference may be made to U.S. Pat. No. 4,036,221 to Hillsman et al. for the details of the construction and operation of one example of such a ventilator. The present invention is used most advantageously with a transportable, or "home care" ventilator. Since most of these home care ventilators employ piston-type pumps, the instant disclosure will refer to the "piston pump" of the ventilator with the understanding that ventilators with functionally-equivalent gas displacement mechanisms (e.g., a bellows) are not to be excluded.

The major elements of the present invention are a demand valve 18 and a blending valve 20. The demand valve 18 has an outlet 22 and an inlet 24 adapted to be fluidly coupled to a compressed gas cylinder 26 having a pressure regulator 28. The cylinder 26 contains a gas at a pressure on the order of 1500 psig, which is regulated down to about 40 to 90 psig by the regulator 28. When the present invention is used in conjunction with a home care ventilator, the gas in the cylinder will be oxygen. Alternatively, the ventilator 10 may be an anesthesia ventilator, in which case the gas will be an anesthetic compound.

Figure 2:
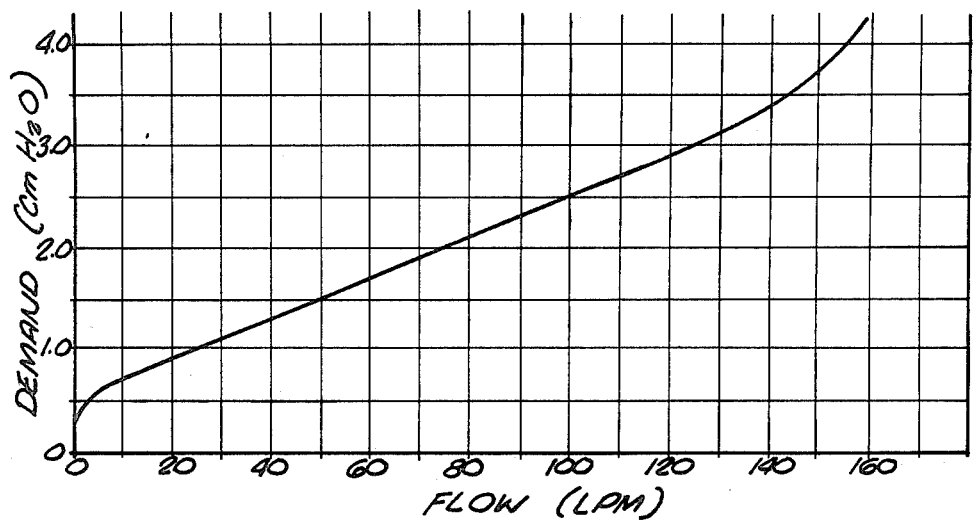
FIG. 2 is a graph of the demand-versus-flow characteristics of a typical demand valve employed in the present invention.

The demand valve 18 may be of any suitable type well-known in the art. For example, a Robertshaw Model 4201 demand valve, manufactured by Robertshaw Controls Company of Anaheim, Calif., has been found to have suitable flow characteristics for use in the present invention. The demand-versus-flow characteristics of this particular valve are shown graphically in FIG. 2. From FIG. 2 it can be seen that the valve 18 "cracks" to permit flow at a demand of about 0.25 $CmH_2O$ applied to its outlet 22, with the flow increasing proportionately with the applied demand until a maximum flow of about 160 lpm is achieved in response to a demand of about 4.25 $CmH_2O$ (with an inlet-side pressure of about 40 psig).

The outlet 22 of the demand valve 18 is fluidly coupled to a first inlet 30 of the blending valve 20, a second inlet 32 of which is open to the ambient atmosphere. The blending valve 20 has a blended gas outlet 34 that is fluidly coupled to a gas intake port 36 on the ventilator 10. The intake port 36, in turn, communicates with the ventilator piston pump 11.

The blending valve 20 has a proportioning mechanism, described in detail below, that selectively adjusts the relative flow capacities of the first inlet 30 and the second inlet 32. This proportioning mechanism is adjusted by a control knob 38.

Still referring to FIG. 1, the general operation of the invention may be easily understood. The piston pump 11 of the ventilator 10 reciprocates back and forth, with a forward inspiratory stroke during which it pumps respiratory gas out of the outlet 13, and a rearward expiratory stroke. The expiratory stroke is in the gas intake phase of the piston pump's operation, during which it draws in a fresh supply of gas through the intake port 36 in preparation for the next inspiratory stroke. It is during this intake phase that the ventilator applies a demand (as defined above) to the blended gas outlet 34 of the blending valve 20. This demand is a function, at least substantially, of the piston's speed during its expiratory stroke. Since the piston accelerates and decelerates during its stroke, the ventilator'demand for gas varies with time during each intake phase. Moreover, the piston's speed of travel may also change in response to a change in the setting of the ventilator's operational controls (e.g., tidal volume, respiration rate, and inspiratory-to-expiratory time ratio). Also, if the ventilator has a "sigh" mode, the piston will exhibit a different volume-versus-time curve during each intake phase preceding a sigh breath delivery.

The blended gas flow extracted from the blended gas outlet 34 in response to the total instantaneous demand applied thereto is the sum of the gas flows into the blending valve through the first inlet 30 and the second inlet 32. The demand valve 18 provides a flow of pressurized gas (e.g., oxygen) into the first inlet 30 in proportion to the demand transmitted to the demand valve outlet 22 via the blending valve first inlet 30. The balance of the gas flow into the blending valve 20 is of the ambient air flowing through the second inlet 32. The total instantaneous blended gas flow emerging from the blended gas outlet 34 is directly proportional to the total instantaneous demand applied to the blended gas outlet 34.

The proportioning mechanism in the blending valve 20 proportion this total demand between the two blending valve inlets 30 and 32, whereby the percentage of the total demand applied to the first inlet 30 (and the demand valve outlet 22 coupled to it) can be selectively varied between a maximum and a minimum. The minimum demand percentage applied by the proportioning mechanism to the first inlet 30 will result in an applied demand level that is less than the demand level necessary to open the demand valve 18. The total flow through the blending valve 20 is thus provided by the air from the second inlet 32. Conversely, when the maximum demand percentage is applied to the first inlet 30, the demand valve 18 is opened to the extent that substantially all of the flow through the blending valve 20 is the gas received from the demand valve 18 via the first inlet 30. As the demand percentage applied to the first inlet 30 is varied from the minimum to the maximum by the proportioning mechanism, the percentage of the total flow from the blended gas outlet 34 contributed by the pressurized gas from the demand valve outlet 22 increases proportionately. Expressed another way, the percentage of the pressurized gas in the total blended gas flow is of proportional to the ratio of the demand applied to the first inlet 30 to the total demand applied to the blended gas outlet 34. Regardless of the demand percentage that is applied to the first inlet 30, the instantaneous flow of blended gas mixture from the blended gas outlet 34 to the ventilator piston pump 11 is proportional to the substantially instantaneous demand applied by the ventilator, throughout the entire gas intake phase of the ventilator's cycle. The percentages of the gases in the blended gas mixture, however, remain substantially constant throughout the gas intake phase. This remains true even if the patient takes a spontaneous breath during the intake phase, since such a spontaneous breath will not appreciably alter the demand applied by the ventilator, due to the very rapid sequencing of the piston pump through the intake phase, as compared to the duration of a spontaneous breath.

The blending valve 20 can be constructed in a variety of ways, two of which are described in detail below. In both of the embodiments to be described, the proportioning mechanism proportions the demand by adjusting the relative flow capacities of the two blending valve inlets, whereby the demand percentage applied to the first inlet 30 is inversely proportional to the ratio of the flow capacity of the second inlet to the flow capacity of the first inlet. Specifically, the first inlet 30 is maintained open at a constant flow capacity, while the second inlet 32 is selectively adjusted between a fully open state and a fully closed state. When the second inlet 32 is fully open, maximizing the aforementioned flow capacity ratio, there is little or no pressure drop across the blending valve 20, leaving essentially a zero or "null" demand applied to the first inlet 30. (There may, in fact, be some measurable demand applied to the first inlet, but not enough to crack the demand valve 18.) Thus, the outflow from the blending valve 20 is essentially 100 percent air from the second inlet 32. As the flow capacity of the second inlet 32 is decreased, a pressure drop across the blending valve increases, creating a proportionately increasing suction or demand applied to the first inlet 30 and thus to the demand valve outlet 22. Thus, as the ratio of the flow capacity of the second inlet 32 to the flow capacity of the first inlet 30 is decreased, the flow through the first inlet 30 from the demand valve 18 will proportionately increase, in accordance with a curve much like that shown in FIG. 2, while the total flow from both inlets together remains substantially constant for a given level of demand applied by the ventilator to the blending valve outlet 34. When the second inlet is fully closed, minimizing the aforementioned flow capacity ratio, all of the demand applied to the blending valve outlet 34 is also applied to the first inlet 30, so that the total flow through the blending valve 20 is provided by the gas flowing from the demand valve 18.

A first preferred embodiment of a blending valve 20 in accordance with the above-described operating principle is shown in FIGS. 3 through 6. This embodiment includes a housing 40 having orifices which define the first inlet 30, the second inlet 32, and the blended gas outlet 34. In the application of oxygen-enrichment for a ventilator, the first inlet 30 receives oxygen from the demand valve 18 (FIG. 1) and may, accordingly, be referred to as the "oxygen inlet". The second inlet 32, or "air inlet", as mentioned above, is open to the ambient atmosphere, advantageously through a filter 42 and a mesh screen 44. The filter 42 may be used to filter out particulate matter, such as dust or pollen that may be suspended in the air. It will create a certain pressure drop across the air inlet 32 for which compensation must be provided in the sizing of the inlet and in the demand/flow characteristics of the demand valve 18.

In this embodiment, the proportioning mechanism is a valving element which comprises a hollow, cylindrical barrel 46 rotatably disposed within the housing 40. The barrel 46 is oriented so that its hollow interior defines an internal passage or bore 48, one end of which is open to the blended gas outlet 34. The barrel has a first orifice 50 in its side wall that registers with the first, or oxygen, inlet 30, and a second orifice 52 in its side wall that is registrable with the second, or air, inlet 32. The first orifice 50 is elongated to encompass a circumferential arc length of at least about 120 degrees, and preferably about 160 to 170 degrees. The second orifice 52 is somewhat smaller than the first orifice 50, and is preferably oval or egg-shaped, for reasons which will be explained below.

The barrel 46 is rotated within the housing 40 by means of the knob 38, which is connected to the closed end of the barrel opposite the outlet 34 by a shaft 54. The shaft 54 carries a radially-extending stop 56. On either side of the shaft 54, extending from the housing 40, are first and second pins 58, 60 which respectively define first and second rotational limits of travel by engagement with the stop 56.

The first orifice 50 is dimensioned so that it maintains its registration with the oxygen inlet 30 throughout the rotation of the barrel 46 between the first and second limits of travel. Thus, a flow path from the oxygen inlet 30 to the outlet 34 via the internal bore 48 is maintained regardless of the rotational position of the barrel 46. The second orifice 52, on the other hand, is dimensioned so that at the first limit of rotational travel, it is in substantially complete registration with the air inlet 32, while at the second limit of travel, the second orifice 52 is completely out of registration with the air inlet, thereby positioning the side wall of the barrel 46 to close the air inlet 32 fully. Thus, at the first limit of travel, the air inlet 32 is fully open, and at the second limit of travel it is fully closed. The oval shape of the second orifice 52 allows the flow capacity of the second inlet 32 to decrease in a substantially linear fashion as the barrel 46 is rotated from the first position to the second position in the direction indicated by the arrow 62 in FIG. 4.

Thus, as the barrel 46 is rotated from the first limit of travel to the second limit of travel, the gas mixture at the outlet 34 gradually changes from 100 percent air from the air inlet 32, to 100 percent oxygen from the oxygen inlet 30, as the demand applied to the latter increases with the decrease in flow through the former. Since air is approximately 21 percent oxygen, the face of the housing between the pins 58 and 60 may be advantageously provided with oxygen percentage indicia calibrated between 21 percent and 100 percent.

Figure 3:
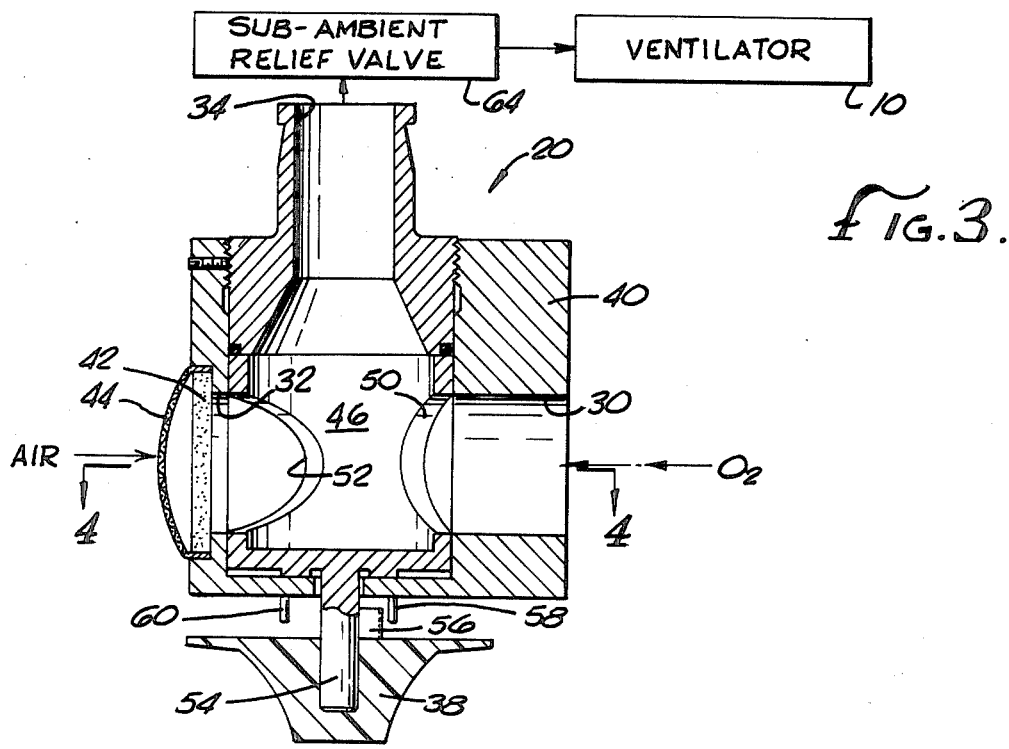
FIG. 3 is a cross-sectional view of a first preferred embodiment of the blending valve used in the present invention, with a schematic representation of a separate sub-ambient relief valve.
Figure 4:
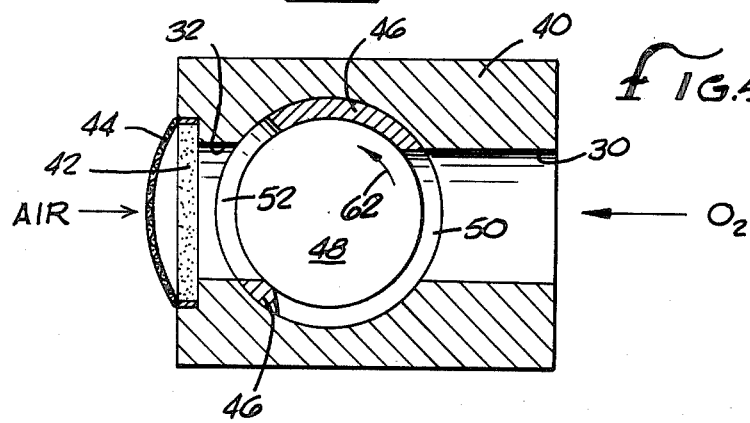
FIG. 4 is a cross-sectional view taken along line 4—4 of FIG. 3.
Figure 5:
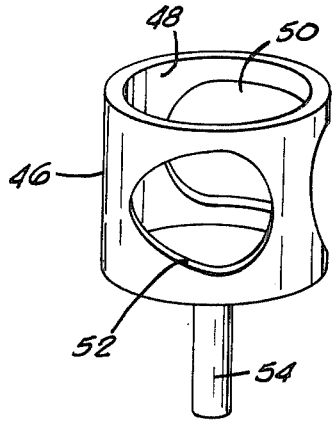
FIG. 5 is a perspective view of the gas-proportioning valving element used in the blending valve embodiment of FIGS. 3 and 4.
Figure 6:
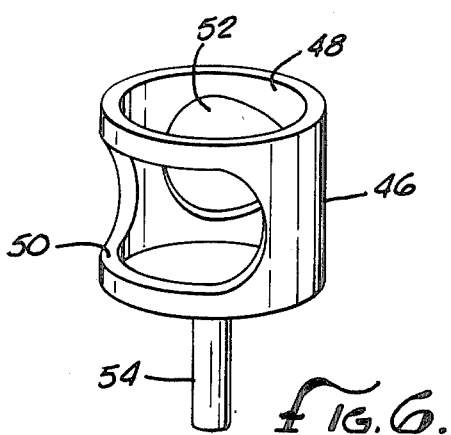
FIG. 6 is a perspective view of the valving element of FIG. 5, showing the element rotated 180 degrees from the position shown in FIG. 5.

As shown in FIG. 3, a sub-ambient relief valve 64 is advantageously provided between the blending valve 20 and the ventilator 10. The sub-ambient relief valve 64 is normally closed, but it opens to provide a flow path from the ambient atmosphere to the ventilator in response to a predetermined level of sub-ambient pressure or demand that is somewhat greater than the maximum demand applied to the blending valve at its maximum gas flow rate. This predetermined demand level is reached only when the air inlet 32 of the blending valve 20 is closed or nearly closed, and the flow of oxygen through the oxygen inlet 30 is partially or totally interrupted. The sub-ambient relief valve thus assures that the ventilated patient receives a life-sustaining supply of air if, for example, the oxygen supply becomes depleted.

Figure 7:
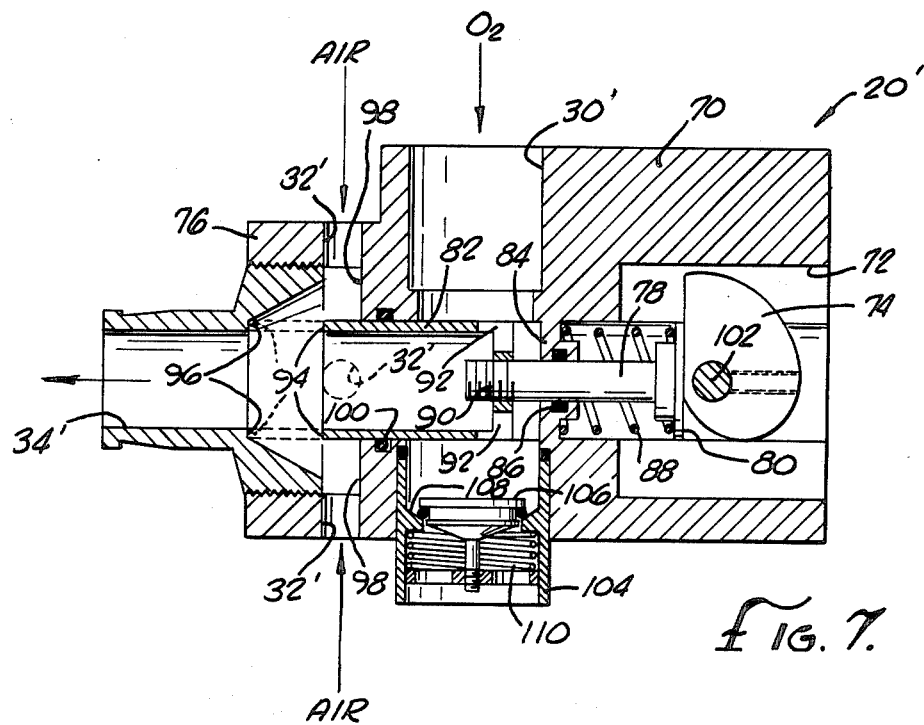
FIG. 7 is a cross-sectional view of a second preferred embodiment of the blending valve used in the present invention.

A second preferred embodiment of the blending valve is shown in FIG. 7, designated by the numeral 20'. This embodiment includes a housing 70 having a large peripheral orifice which defines an oxygen inlet 30'. The housing has a proximal end having a chamber 72 that accommodates a rotational cam 74. The distal end of the housing 70 is formed as a cylindrical neck 76 having a plurality of circumferentially-spaced peripheral holes, each defining an air inlet 32'. The plural air inlets 32' are in communication with a blended gas outlet 34' extending from the distal end of the housing 70, through the neck 76.

In this embodiment, the proportioning mechanism is a valving element which comprises a rod 78 with a proximal end formed as a cam follower surface 80, and a distal end to which is attached a hollow cylindrical occlusion member 82. The rod 78 is supported for axial movement in the housing 70 by a rod journal ring 84 having an internal peripheral groove that advantageously carries an O-ring seal 86. The rod journal ring 84 is preferably integral with the interior surface of the housing, forming a shoulder therewith against which is seated the distal end of a coil spring 88. The proximal end of the coil spring 88 bears against the distal side of the cam follower surface 80, urging the latter into engagement against the cam 74.

The occlusion member 82 is advantageously attached to the distal end of the rod 78 by threads 90, but it also may formed as an integral unit with the rod. The occlusion member 82 has a proximal end that is provided with a plurality of peripheral orifices 92 that communicate with the hollow interior of the occlusion member, providing a flow path from the oxygen inlet 30', through the orifices 92 and he occlusion member interior, band finally to the outlet 34'. The distal end of the occlusion member 82 defines a substantially annular sealing surface 94, the latter being engageable against an annular seat 96 defined around the interior entrance of the outlet 34'. The occlusion member 82 passes through a close-tolerance opening in a barrier member 98 that separates the oxygen inlet 30' from the air inlets 32', and that defines the proximal end of the neck 76. This close-tolerance opening may advantageously be sealed by an O-ring 100.

In operation, the cam 74 is rotated by a shaft 102, the other end of which is attached to a knob (not shown), which may be similar to the knob 38 of the previously-described embodiment. The rotation of the cam 74 causes the rod 78 and the occlusion member 82 to reciprocate axially between two limits of travel by the engagement of the cam against the cam follower surface 80. At the first limit of travel, shown in solid outline in FIG. 7, the occlusion member 82 is at a position closest to the proximal end of the housing 70. In this position, the air inlets 32' are unobstructed by the occlusion member 82, leaving them fully open to the outlet 34'. There is thus an unobstructed flow path between the air inlets and the outlet and between the oxygen inlet and the outlet. As the occlusion member 82 is moved distally by the rotation of the cam 74, the air inlets 32' are progressively obstructed, thereby decreasing their flow capacity and thus increasing the demand applied to the oxygen inlet 30', as previously described. At the distal limit of travel, the sealing surface 94 of the occlusion member 82 seats against the annular seat 96, as shown in broken outline in FIG. 7, thereby totally blocking the flow from the air inlets 32'.

Thus, at the proximal limit of travel, with the air inlets completely open, the flow through the valve is substantially 100 percent air from the air inlets 32', while at the distal limit of travel, with air inlets fully closed, the flow is substantially 100 percent oxygen from the oxygen inlet 30', in accordance with the previously-described operational principles. At positions between these two limits of travel, the ratio of air to oxygen in the blended gas mixture in the outlet 34' gradually decreases as the occlusion member 82 moves distally. The cam 74 is advantageously shaped to allow the flow capacity of the air inlets 32' to diminish in a substantially linear fashion as the occlusion member 82 moves distally. As in the first blending valve embodiment, oxygen percentage indicia may be employed, with the oxygen percentage calibrated from 21 percent (pure air) to 100 percent.

In this second embodiment, an integral sub-ambient relief valve 104 may be built into the valve housing 70. Functionally, it may be identical to th discrete sub-ambient relief valve 64 used in conjunction with the previously-described embodiment. The design of the sub-ambient relief valve 104 is conventional, comprising a valving element 106 biased closed against a valve seat 108 by a coil spring 110. The valving element opens inwardly against the force of the spring in response to a predetermined demand level, as previously described, to open an alternate flow path from the atmosphere to the outlet 34' when the air inlets 32' are shut, or nearly shut.

From the foregoing description, it will be appreciated that the present invention provides a number of significant advantages over prior art blending systems. Specifically, a gas blending system in accordance with the present invention provides blended gas to the ventilator at a flow rate that is proportional to the substantially instantaneous demand applied by the ventilator's piston pump, while maintaining the preselected gas mixture proportions substantially constant through the changes in demand applied over the gas intake phase of the piston pump cycle. Moreover, the blended gases are thoroughly mixed within the piston pump itself, by virtue of the gas blending system being placed upstream from the ventilator. Thus, there is no need for separate mixing apparatus. Furthermore, the pressurized gas (e.g., oxygen) is consumed on demand only, thereby minimizing both wastage and potential safety problems due to leakage. Accurate and repeatable control of the blend proportions is also achieved, throughout a full range of mixtures, from 100 percent air to 100 percent pressurized gas (e.g., oxygen).

The aforementioned advantages are provided by a system that has only a single, easily-operated control, and that is readily adaptable to a wide variety of applications. For example, as mentioned at the outset, the system will work with a bellows-type ventilator, such as is typically used to administer anesthetic gas to a surgical patient. In this application, the pressurized gas will be nitrous oxide, halane, or some other suitable anesthetic. In such an application, the accurate mixture control and minimal leakage exhibited by the present invention will be particularly advantageous.

It will be readily appreciated by those skilled in the pertinent arts that the specific embodiments of the invention described above are exemplary only, and that various modifications and variations may be devised.

For example, the specific blending valve structures described herein may be modified to suit various different types of ventilators, while retaining the same general operational principles. Such modifications and variations should thus be considered within the spirit and scope of the invention, as defined in the claims which follow.

What is claimed is:

1. A gas blending system for blending two gases in response to a sub-ambient demand applied by a ventilator or the like, said gas blending system comprising:
positive displacement gas pump means for periodically creating said sub-ambient demand;
demand valve means, having an outlet, and an inlet adapted to be coupled to a pressure-regulated supply of a first gas, for providing a flow of said first gas from said inlet to said outlet, in proportion to the demand experienced by said outlet; and
a blending valve, having a first inlet coupled to the outlet of said demand valve means, a second inlet coupled to a substantially ambient-pressure supply of a second breathable gas, and a blended gas outlet adapted to be fluidly coupled to said gas pump means, wherein said blending valve includes proportioning means for selectively adjusting the relative flow capacities of said first and second inlets;
whereby, when said inlet of said demand valve means is coupled to a pressure-regulated supply of a first gas, and said blended gas outlet is coupled to said gas pump means, the total blended gas flow through said blended gas outlet is proportional to the total demand applied to said blended gas outlet by said gas pump means, and whereby the percentage of said first gas in said total blended gas flow is proportional to the ratio of the demand applied to said first blending valve inlet to the total demand applied to said blended gas outlet.

2. The gas blending system of claim 1, wherein said proportioning means maintains said first inlet at substantially a constant flow capacity while varying the flow capacity of said second inlet.

3. The gas blending system of claim 1, wherein the demand applied to said first inlet is inversely proportional to the ratio of the flow capacity of said second inlet to the flow capacity of said first inlet.

4. The gas blending system of claim 3, wherein the demand applied to said first inlet is approximately equal to said total demand applied to said blended gas outlet when said ratio is at its minimum, and approximately equal to a substantially null demand when said ratio is at its maximum.

5. The gas blending system of claim 4, wherein the demand applied to said first inlet increases from said substantially null demand to said total demand as said flow capacity ratio is varied from its maximum to its minimum.

6. The gas blending system of claim 2, wherein said proportioning means selectively varies said second blending valve inlet between a fully closed state and a fully open state, whereby the demand applied to said first blending valve inlet is varied from said total demand to a substantially null demand as said second inlet is varied from said fully closed state to said fully open state.

7. The gas blending system of claim 1, further comprising relief valve means for admitting ambient air into said ventilator in response to a predetermined subambient pressure applied to said blending valve.

8. The gas blending system of claim 7, wherein said blending valve includes said relief valve means.

9. The gas blending system of claim 6, wherein said blending valve includes a housing having first and second inlets simultaneously communicating with said blended gas outlet, and wherein said proportioning means comprises:
a valving element in said housing, operatively associated with said second inlet, said valving element being movable between a first position in which said second inlet is in a fully open state, and a second position in which said second inlet is in said fully closed state, whereby said first inlet is fully open throughout the path of travel of said valving element, and whereby the demand applied to said first inlet as a percentage of said total demand is inversely proportional to the degree of opening of said second inlet, as determined by the position of said valving element.

10. The gas blending system of claim 9, wherein said blending valve includes a rotatable cam, and wherein said valving element comprises:
a rod having a proximal end and a distal end, said proximal end being engaged against said cam; and
occlusion means, on the distal end of said rod, for movement between said first and second positions by the rotation of said cam, said second inlet being substantially unobstructed when said occlusion means is in said first position, and substantially fully occluded when said occlusion means is in said second position.

11. The gas blending system of claim 9, wherein said valving element comprises:
a rotatable barrel having a substantially cylindrical wall that defines an internal bore which communicates with said blended gas outlet;
a first orifice in said wall that registers with said first inlet to provide communication between said first inlet and said bore; and
a second orifice in said wall that is registrable with said second inlet to provide communication between said second inlet and said bore;
whereby said barrel is rotatable between said first and second positions, said second orifice being in substantially complete registration with said second inlet when said barrel is in said first position, and the wall of said barrel occluding said second inlet when said barrel is in said second position, said first orifice substantially maintaining its registration with said first inlet as said barrel is rotated between said first and second positions.

12. A gas blending system for controllably blending a pressure-regulated gas with ambient air in response to a sub-ambient demand applied by a ventilator or the like, said system comprising:
positive displacement gas pump means for periodically creating said sub-ambient demand;
demand valve means having an inlet for receiving said pressure-regulated gas and an outlet for discharging a flow of said gas in response to a demand applied thereto;
blending valve means, having a first inlet coupled to said outlet of said demand valve means, a second inlet for receiving ambient air, and a blended gas outlet adapted to be coupled to said gaspump means; and
proportioning means, operatively associated with said blending valve means, for selectively controlling the relative proportions of said pressre-regulated gas and ambient air flowing into said blending valve means through said first and second inlets, respectivley, said proportioning means being position-adjustable between first and second limits of travel;

whereby the total blended gas flow through said blended gas outlet is proportional to the total demand applied thereto by said gas pump means, and whereby the relative proportions of said pressure-regulated gas and ambient air in said blended gas flow are determined substantially solely by the position of said proportioning means.

13. The gas blending system of claim 12, wherein said proportioning means, at said first limit of travel, provides a maximum ratio of ambient air to said pressure-regulated gas, and at said second limit of travel, provides a minimum ratio of ambient air to said pressure-regulated gas.

14. The gas blending system of claim 13, wherein said proportioning means selectively varies the flow capacity of said second inlet between a maximum and a minimum as said proportioning means is adjusted between said first position and said second position, while the flow capacity of said first inlet is maintained substantially constant.

15. The gas blending system of claim 14, wherein the demand that is applied to said demand valve means outlet through said blending valve means first inlet as a percentage of said total demand is inversely proportional to the flow capacity of said blending valve means second inlet.

16. The gas blending system of claim 15, wherein said proportioning means selectively varies said second inlet between a fully closed state and a fully open state, whereby the demand applied to said demand valve means outlet through said blending valve means first inlet is varied from the total demand applied to said blended gas outlet by said ventilator or the like to a substantially null demand as said second inlet is varied from said fully closed state to said fully open state.

17. The gas blending system of claim 12, further comprising relief valve means operatively associated with said blending valve means, for admitting ambient air into said ventilator or the like when said proportioning means is at or near said second limit of travel and a predetermined demand level is applied to said blended gas outlet.

18. The gas blending system of claim 12, wherein said blending valve means comprises a housing containing said proportioning means and including said blended gas outlet and said first and second inlets, and wherein said proportioning means comprises:

a rotatable barrel having an internal bore that communicates with said blended gas outlet, said barrel being mounted in said housing for rotation between said first and second limits of travel;

a first orifice in said barrel that registers with said first inlet to provide communication between said first inlet and said bore; and a second orifice in said barrel that is registrable with said second inlet to provide communication between said second inlet and said bore;

whereby said second orifice is in substantially complete registration with said second inlet when said barrel is at said first limit of travel, and wherein said barrel substantially totally occludes said second inlet when said barrel is at said second limit of travel, said first orifice substantially maintaining its registration with said first inlet as said barrel is rotated between said first and second limits of travel.

19. The gas blending system of claim 12, wherein said blending valve means comprises a housing containing said proportioning means and including said blended gas outlet and said first and second inlets simultaneously communicating with said outlet, and wherein said proportioning means is operatively associated with said second inlet and comprises:

a rotatable cam;

a rod having a proximal end and a distal end, said proximal end being engaged against said cam; and occlusion means, on said distal end of said rod, for movement between said first and second limits of travel by the rotation of said cam, said second inlet being substantially unobstructed when said occlusion means is at said first limit of travel, and substantially fully occluded when said occlusion means is at said second limit of travel.

20. A gas blending system for controllably blended a pressure-regulated gas with ambient air in response to a sub-ambient demand applied by a ventilator or the like, said system comprising:

positive displacement gas pump means for periodically creating said sub-ambient demand;

a demand valve having an inlet for receiving said pressure-regulated gas and an outlet for discharging a flow of said gas in proportion to the demand applied thereto;

gas blending means having a first inlet coupled to said demand valve outlet, a second inlet open to the ambient atmosphere, and a blended gas outlet adapted to be fluidly coupled to said gas pump means, whereby a flow of the gases received from said first and second inlet is discharged through said blended gas outlet in response to the total demand applied thereto by said gas pump means; and proportioning means, in said gas blending means, for adjustably varying the percentage of the total demand applied to said blended gas outlet which is transmitted to said demand valve outlet through said first gas blending means inlet, said proportioning means being adjustable between a first position in which a minimum percentage of the total demand is applied to said demand valve outlet, and a second position in which a maximum percentage of the total demand is applied to said demand valve outlet;

whereby the total blended gas flow from said blended gas outlet is proportional to the total demand applied thereto, and whereby the relative proportions of said pressure-regulated gas and ambient air in said blended gas flow are determined by the position of said proportioning means.

21. The gas blending system of claim 20, wherein the relative proportions of said pressure-regulated gas and ambient air in said blended gas flow are substantially independent of the total demand applied to said blended gas outlet.

22. The gas blending system of claim 21, wherein said proportioning means adjustably varies the relative flow capacities of said first and second gas blending means inlets, whereby the flow capacity of said second inlet is adjusted from a fully open state to a substantially fully closed state as said proportioning means is adjusted from said first position to said second position, the flow capacity of said first inlet being maintained substantially constant throughout the adjustment of said proportioning means.

23. The gas blending system of claim 22, wherein substantially none of the total demand is transmitted to said demand valve outlet when said second inlet is in said fully open state and wherein substantially all of the total demand is transmitted to said demand valve outlet when said second inlet is in said substantially fully closed state.

24. The gas blending system of claim 23, wherein the demand that is transmitted to said demand valve outlet as a percentage of said total demand is inversely proportional to the flow capacity of said second inlet.

25. The gas blending system of claim 20, wherein said gas blending means comprises a housing containing said proportioning means and including said first and second inlets and said blended gas outlet, and wherein said proportioning means comprises:
- a rotatable barrel having an internal bore that communicates with said blended gas outlet, said barrel being mounted in said housing for rotation between said first and second positions;
- a first orifice in said barrel that registers with said first inlet to provide communication between said first inlet and said bore; and
- a second orifice in said barrel that is registrable with said second inlet to provide communication between said second inlet and said bore;
- whereby said second orifice is in substantially complete registration with said second inlet when said barrel is in said first position, and wherein said barrel substantially totally occludes said second inlet when said barrel is in said second position, said first orifice substantially maintaining its registration with said first inlet as said barrel is rotated between said first and second positions.

26. The gas blending system of claim 20, wherein said gas blending means comprises a housing containing said proportioning means and including said first and second inlets simultaneously communicating with said blended gas outlet, and wherein said proportioning means is operatively associated with said second inlet and comprises:
- a rotatable cam;
- a rod having a proximal and a distal end, said proximal end being engaged against said cam; and
- occlusion means, on said distal end of said rod, for movement between said first and second positions by the rotation of said cam, said second inlet being substantially unobstructed when said occlusion means is in said first position, and substantially fully occluded when said occlusion means is in said second position.

27. The gas blending system of claim 20, further comprising relief valve means, operatively associated with said gas blending means, for admitting ambient air into said ventilator or the like when said proportioning means is at or near said first position and a predetermined demand level is applied to said blended gas outlet.

* * * * *

UNITED STATES PATENT AND TRADEMARK OFFICE
CERTIFICATE OF CORRECTION

PATENT NO. : 4,702,240

DATED : October 27, 1987

INVENTOR(S) : SAMIR M. CHAOUI

It is certified that error appears in the above-identified patent and that said Letters Patent is hereby corrected as shown below:

Column 1, line 35 after the word "oxygen", delete "has been the lack".

Column 6, line 66, delete the word "of" first occurrence.

Column 9, line 37, change "band" to --and--.

Column 9, line 37, change "he" to --the--

Signed and Sealed this

Seventh Day of June, 1988

Attest:

DONALD J. QUIGG

Attesting Officer

Commissioner of Patents and Trademarks